(12) United States Patent
Communi et al.

(10) Patent No.: US 7,485,703 B2
(45) Date of Patent: Feb. 3, 2009

(54) ANTIBODY AGAINST G-PROTEIN COUPLED RECEPTOR SHOWING SELECTIVE AFFINITY FOR ATP AND USES THEREFOR

(76) Inventors: Didier Communi, Groendullaan 19, Vilvoorde (BE) B-1800; Jean-Marie Boeynaems, Avenue Peter Benoit 5, Wemmel (BE) B-1780

( * ) Notice: Subject to any disclaimer, the term of this patent is extended or adjusted under 35 U.S.C. 154(b) by 0 days.

(21) Appl. No.: 11/384,733

(22) Filed: Mar. 20, 2006

(65) Prior Publication Data
US 2006/0160149 A1    Jul. 20, 2006

Related U.S. Application Data

(60) Continuation of application No. 10/977,395, filed on Oct. 29, 2004, now Pat. No. 7,288,631, which is a division of application No. 10/152,058, filed on May 21, 2002, now Pat. No. 7,045,345, which is a continuation of application No. 09/254,783, filed on Aug. 16, 1999, now abandoned, which is a continuation of application No. PCT/BE98/00108, filed on Jul. 9, 1998.

(30) Foreign Application Priority Data
Jul. 9, 1997    (EP) ................. 9787010

(51) Int. Cl.
*C07K 16/28*    (2006.01)
*C07K 14/705*   (2006.01)
(52) U.S. Cl. ................. 530/388.22; 424/143.1
(58) Field of Classification Search ................. None
See application file for complete search history.

(56) References Cited
U.S. PATENT DOCUMENTS
5,011,912 A * 4/1991 Hopp et al. ............. 530/387.9

* cited by examiner

*Primary Examiner*—John D Ulm
(74) *Attorney, Agent, or Firm*—Edwards Angell Palmer & Dodge LLP; Kathleen Williams; Jeffrey Kopacz

(57) ABSTRACT

The present invention relates to isolated antibodies both polyclonal and monoclonal, that specifically bind to a G-protein coupled receptor showing selective affinity for ATP. The invention further comprises a pharmaceutical composition comprising antibodies that specifically bind to the G-protein coupled receptor showing selective affinity for ATP.

5 Claims, 9 Drawing Sheets

P2Y₁₁ sequence

```
                                         M   G   Q   S   G   R   S         7
  1 GAATTCGGCACGAGGAGGCCTCGTGGAGGACACAGTCAGGGAGGTCC                        60

R   H   Q   K   R   A   R   A   Q   A   Q   L   R   N   L   E   A   Y   A   A    27
  8                                                                       
 61 CGGCACCCAGAAGCGCGCCCGCGCCCAGGCGCAGCTCCGCAACCTCGAGGCCTATGCCGCG          120

N   P   H   S   F   V   F   T   R   G   C   T   G   R   N   I   R   Q   L   S    47
 28                                                                       
121 AACCCGCACTCGTTCGTGTTCACGCGAGGCTGCACGGGTCGCAACATCCGGCAGCTCAGC          180

L   D   V   R   R   V   M   E   P   L   T   A   S   R   L   Q   V   R   K   K    67
 48                                                                       
181 CTGGACGTGCGGCGGGTCATGGAGCCGCTCACTGCCAGCCGTCTGCAGGTTCGTAAGAAG          240

N   S   L   K   D   C   V   A   V   A   G   P   L   G   V   T   H   F   L   I    87
 68                                                                       
241 AACTCGCTGAAGGACTGCGTGGCAGTGGCCGGCCCTCGGGGTCACACACTTTCTGATC            300

L   S   K   T   E   T   N   V   Y   F   K   L   M   R   L   P   G   G   P   T    107
 88                                                                       
301 CTGAGCAAAACAGAGACCAATGTCTACTTTAAGCTGATGCGCCTCCCAGGAGGCCCCACC         360

L   T   F   Q   V   K   K   Y   S   L   V   R   D   V   V   S   S   L   R   R    127
108                                                                       
361 TTGACCTTCCAGGTGAAGAAGTACTCGCTGGTGCGTGATGTGGTCTCCTCACTGCGCCGG         420

H   R   M   H   E   Q   Q   F   A   H   P   P   L   L   V   L   N   S   F   G    147
128                                                                       
421 CACCGCATGCACGAGCAGCAGTTTGCCCACCCTCCTCTGGTACTCAACAGCTTTGGC            480
```

FIGURE 1A

| | | | |
|---|---|---|---|
| 148 | P H G M H V K L M A T M F Q N L F P S I | 167 | |
| 481 | CCCATGGTATGCATGTGAAGCTCATGGCCACCATGTTCCAGAACCTGTTCCCCTCCATC | 540 | |
| 168 | N V H K V N L N T I K R C L L I D Y N P | 187 | |
| 541 | AACGTGCACAAGGTGAACCTGAACACCATCAAGCGCTGCCTCCTCATCGACTACAACCCC | 600 | |
| 188 | D S Q E L D F R H Y S I K V V P V G A S | 207 | |
| 601 | GACTCCCAGGAGCTGGACTTCCGCCACTATAGCATCAAAGTTGTTCCTGTGGGCGAGT | 660 | |
| 208 | R G M K K L L Q E K F P N M S R L Q D I | 227 | |
| 661 | CGCGGGATGAAGAAGCTGCTCCAGGAGAAGTTCCCAACATGAGCCGCCTGCAGGACATC | 720 | |
| 228 | S E L L A T G A G L S E S E A E P D G D | 247 | |
| 721 | AGCGAGCTGCTGGCCACGGGCGCGGGGCTGTCGGAGAGCGAGGCAGAGCCTGACGGCGAC | 780 | |
| 248 | H N I T E L P Q A V A G R G N M R A Q Q | 267 | |
| 781 | CACAACATCACAGAGCTGCCTCAGGCTGTGCGGCCGCCCCAGCAG | 840 | |
| 268 | S A V R L T E I G P R M T L Q L I K V Q | 287 | |
| 841 | AGTGCAGTGCGGCTCACCGAGATCGGCCCGCGGATGACACTGCAGCTCATCAAGGTCCAG | 900 | |
| 288 | E G V G E G K V M F H S F V S K T E E E | 307 | |
| 901 | GAGGGCGTCGGGGAGGGCAAAGTGATGTTCCACAGTTTTGTGAGCAAGACGGAGGAGGAG | 960 | |
| 308 | L Q A I L E A K E K K L R L K A Q R Q A | 327 | |
| 961 | CTGCAGGCCATCCTGGAAGCCAAGGAGAAGAAGCTGCGTCTGAAGGCGCAGAGGCAGGCC | 1020 | |
| 328 | Q Q A Q N V Q R K Q E Q R E A H R K K S | 347 | |
| 1021 | CAGCAGGCCCAGAATGTGCAGCGCAAGCAGGAGCAGAGGGAGGCCCACAGAAAGAAGAGC | 1080 | |

FIGURE 1B

```
348  L  E  G  M  K  K  K  A  R  V  G  G  S  D  E  E  A  S  G  I  P              367
1081 CTGGAGGGCATGAAGAAGAAGGCACGGGTCGGGGGTAGTGATGAAGAGGCCTCTGGGATCCCT            1140

368  S  R  T  A  S  L  E  L  G  E  D  D  D  D  E  Q  E  D  D  D  I              387
1141 TCAAGGACGGCGAGCCTGGAGTTGGGTGAGGACGATGACGATGAACAGGAAGATGATGACATC            1200

388  E  Y  F  C  Q  A  V  G  E  A  P  S  E  D  L  F  P  E  A  K                 407
1201 GAGTATTTCTGCCAGGCGGTGGGCGAGGCGCCCAGTGAGGACCTGTTCCCCGAGGCCAAG               1260

408  Q  K  R  L  A  K  S  P  G  R  K  R  K  R  W  E | M  D  R  G                427
1261 CAGAAACGGCTTGCCAAGTCCCAGGGCGGAAGCGGTGGGAAATGGATCGAGGT                      1320

428  A  K  S  C  P  A  N  F  L  A  A  D  D  K  L  S  G  F  Q                    447
1321 GCCAAGTCCTGCCCTGCCAACTTCTTGGCAGCTGCCGACGACAAACTCAGTGGGTTCCAG               1380

448  G  D  F  L  W  P  I  L  V  E  F  L  V  A  S  N  G                          467
1381 GGGGACTTCCTGTGGCCCATACTGGTGGTTGAGTTCCTGGTGGCCAGCAATGGC                    1440

468  L  A  L  Y  R  F  S  I  R  K  Q  R  P  W  H  P  A  V  V  F                 487
1441 CTGGCCCTGTACCGCTTCAGCATCCGGAAGCAGCGCCCATGGCACCCCGCCGTGGTCTTC              1500

488  S  V  Q  L  A  V  S  D  L  L  C  A  L  T  L  P  P  L  A  A                 507
1501 TCTGTCCAGCTGGCAGTCAGCGACCTGCTCTGCGCTCTGACCCTGCCCCCGCTGGCCGCC              1560

508  Y  L  Y  P  P  K  H  W  R  Y  G  E  A  A  C  R  L  E  R  F                 527
1561 TACCTCTATCCCCCCAAGCACTGGCGCTATGGGGAGGCCGCCTGCCGCCTGGAGCGCTTC              1620
```

FIGURE 1C

```
528   L   F   T   C   N   L   L   G   S   V   I   F   I   T   C   I   S   L   N   R      547
1621  CTCTTCACCTGCAACCTGCTGGGCAGCGTCATCTTCATCACCTGCATCAGCCTCAACCGC                          1680

548   Y   L   G   I   V   H   P   F   F   A   R   S   H   L   R   P   K   H   A   W      567
1681  TACCTGGGCATCGTGCACCCCTTCTTCGCCCGAAGCCACCTGCGACCCAAGCACGCCTGG                          1740

568   A   V   S   A   A   G   W   V   L   A   A   L   L   A   M   P   T   L   S   F      587
1741  GCCGTGAGCGCTGCCGGCTGGGTCCTGGCCGCCCTGCTGGCCATGCCCACTCTCAGCTTC                          1800

588   S   H   L   K   R   P   P   Q   Q   G   A   G   ■   C   S   V   A   R   P   E      607
1801  TCCCACCTGAAGAGGCCGCCGCAGCAGGGGGCAGGGCAACTGCAGCGTGGCCAGGCCCGAG                         1860

608   A   C   I   K   C   L   G   T   A   D   H   G   L   A   A   Y   R   A   Y   S      627
1861  GCCTGCATCAAGTGTCTGGGGACAGACAGAGGGCTGGCGGCCTACAGAGCGTATAGC                             1920

628   L   V   L   A   G   L   G   C   G   L   P   L   L   L   T   L   A   A   Y   G      647
1921  CTGGTGCTGGCCGGGTTGGGCTGTGGCCTGCCGCTGCTGCTCACGCTGGCAGCCTACGGC                          1980

648   A   L   G   R   A   V   L   R   S   P   G   M   T   V   A   E   K   L   R   V      667
1981  GCCCTCGGGCGCGCAGTGCTACGCAGCCCAGGCATGACTGTGGCCGAGAAGCTGCGTGTG                          2040

668   A   A   L   V   A   S   G   V   A   L   Y   A   S   S   Y   V   P   Y   E   I      687
2041  GCAGGCGTTGGTGGCCAGTGGTGTGGCCCTCTACGCCAGTTCCTATGTGCCCTACCACATC                         2100

688   M   R   V   L   N   V   D   A   R   R   W   S   T   R   C   P   S   F   A          707
2101  ATGCGGGTGCTCAACGTGGATGCTCGGCGCTGGAGCACCCGCTGCCCGAGCTTTGCA                             2160

708   D   I   A   Q   A   T   A   A   L   E   L   G   P   Y   V   G   Y   Q   V   M      727
2161  GACATAGCCCAGGCCACAGCCGCCCTGGAGCTCGGCCCCTACGTGGGCTACCAGGTGATG                          2200
```

FIGURE 1D

```
728   R  G  L  M  P  L  A  F  C  V  H  P  L  L  Y  M  A  A  V  P    747
2221  CGGGGCCTCATGCCCCTGGCCTTCTGTGTCCACCCTCTACTCTACATGGCCGCAGTGCCC   2280

748   S  L  G  C  C  C  R  H  C  P  G  Y  R  D  S  W  N  P  E  D    767
2281  AGCCTGGGCTGCTGCTGCCGACACTGCCCCGGCTACAGGGACAGCTGGAACCCAGAGGAC   2340

768   A  K  S  T  G  Q  A  L  P  L  N  A  T  A  A  P  K  P  S  E    787
2341  GCCAAGAGCACTGGCCAAGCCCTGCCCCTCAATGCCACAGCCGCCCCTAAACCGTCAGAG   2400

788   P  Q  S  R  E  L  S  Q  *
2401  CCCCAGTCCCGTGAGCTGAGCTGA
```

ANTIBODY AGAINST G-PROTEIN COUPLED RECEPTOR SHOWING SELECTIVE AFFINITY FOR ATP AND USES THEREFOR

CROSS-REFERENCE TO RELATED APPLICATION

The present invention is a Continuation of U.S. application Ser. No. 10/977,395, filed Oct. 29, 2004, which is a divisional of U.S. application Ser. No. 10/152,058, filed May 21, 2002, which is a continuation of U.S. application Ser. No. 09/254,783, filed Aug. 16, 1999, which is a continuation of PCT/BE98/00108, filed Jul. 9, 1998, which claims priority to EP97870101.9, filed Jul. 9, 1997. The contents of each priority application is incorporated by reference herein in its entirety.

OBJECT OF THE PRESENT INVENTION

The present invention concerns a new G protein-coupled receptor having selective affinity for ATP and the nucleic acid molecule encoding said receptor, vectors comprising said nucleic acid molecule, cells transformed by said vector, antibodies directed against said receptor, nucleic acid probes directed against said nucleic acid molecule, pharmaceutical compositions comprising said products and non human transgenic animals expressing the receptor according to the invention or the nucleic acid molecule according to said receptor.

BACKGROUND OF THE INVENTION

An impressive number of P2 receptors subtypes has been cloned since 1993. A new molecular nomenclature has then been created in which G protein-coupled P2 receptors have been named P2Y while P2 receptors having an intrinsic ion channel activity have been named P2X. The P2Y family encompasses selective purinoceptors (the $P2Y_1$ receptor activated by ATP and ADP), nucleotide receptors responsive to both adenine and uracil nucleotides ($P2Y_2$ receptor: activated equipotentally by ATP and UTP) and pyrimidinoceptors (the $P2Y_3$ and $P2Y_6$ receptors activated by UDP; the $P2Y_4$ receptor: activated by UTP). The $P2Y_5$ and $P2Y_7$ receptors display limited homologies with the other members of the P2Y family. They have been included in this family especially on the basis of radioligand binding studies showing affinities for adenine nucleotides (1-18).

SUMMARY OF THE INVENTION

The present invention concerns a new receptor having the amino acids sequence of FIG. 1 (SEQ ID NO: 1) or any receptor which presents more than 50%, preferably more than 70%, more preferably more than 85%, more specifically more than 95% homology with the amino acids sequence of FIG. 1 (SEQ ID NO: 1).

The present invention concerns also the receptor having at least the amino acids sequence of FIG. 1 (SEQ ID NO: 1) or a portion thereof, preferably an amino acids sequence wherein the large extracellular part (the $NH_2$ portion of 450 amino acids sequence the end of which (♦) is represented on FIG. 1 (SEQ ID NO: 1); note that the amino acid numbering of FIG. 1 is incorrect: i.e., residue number 437 in FIG. 1 is correctly numbered as residue 424 in SEQ ID NO: 1) has been truncated or active parts of said portion such as the sixth and seventh transmembrane domains comprising the amino acids: $His^{686}$, $Arg^{689}$ and $Arg^{728}$.

The present invention is also related to said $NH_2$ portion of 450 amino acids sequence, including peptides reproducing or mimicking a portion of this sequence or of organic molecules sharing the effects of these peptides.

Indeed, the inventors have discovered that either the whole receptor having the amino acids sequence of FIG. 1 or its portion (preferably the amino acids sequence wherein the large extracellular part of 450 amino acids has been truncated and starting from (♦) in FIG. 1) seems to have the same industrial application (said portion will be identified hereafter as the $P2Y_{11}$ receptor or sequence).

The first industrial application of this receptor or its portions is the screening of agonists and antagonists of said receptor which may have advantageous pharmaceutical or diagnostical properties. The second industrial application of the receptor according to the invention or of its portions or of active parts of its portions is the identification of patients who may present genetic disorders induced by an inactive receptor or by an inactive portion of said receptor.

According to a preferred embodiment of the present invention, said receptor is a human receptor.

ATP seems to be the preferential natural agonist of this receptor: UTP, UDP, $AP_4A$, $AP_6A$, AMP and adenosine seem to be unable to stimulate the phosphoinositide pathway or were much less potent that ATP.

Therefore, the invention is also related to a new G-coupled receptor, its portions or active parts of its portions having a selective affinity for ATP. "A selective affinity for ATP" means that ATP is able to induce the formation of a functional response (preferably the accumulation of Inositol triphosphate $IP_3$ and a rise of intracellular $Ca^{2+}$) in a short time of incubation with said agonist (preferably in less than 5 min; more preferably less than 1 min) while the other known agonists of P2Y (UTP, UDP, $AP_4A$, $AP_6A$, AMP and adenosine) were unable to stimulate said receptor or were much less potent than ATP and induce a detectable functional response by said receptor.

The present invention is also related to a nucleic acid molecule, such as a DNA molecule or an RNA molecule, encoding the receptor, its portions or active parts of its portions according to the invention.

Preferably, said DNA molecule is a cDNA molecule or a genomic DNA molecule.

Preferably, said nucleic acid molecule has more than 50%, preferably more than 70%, more preferably more than 85%, more specifically more than 95% homology with the DNA sequence shown in FIG. 1.

Preferably, the invention is related to a nucleic acid molecule which has more than 50%, preferably more than 70%, more preferably more than 85%, more specifically more than 95% homology with this DNA sequence (shown in FIG. 1), wherein the DNA sequence encoding the 450 amino acids of the $NH_2$ portion were truncated.

The present invention is also related to the vector comprising the nucleic acid molecule according to the invention. Preferably, said vector is adapted for expression in a cell and comprises the regulatory elements necessary for expressing the amino acid molecule in said cell operatively linked to the nucleic acid sequence according to the invention as to permit expression thereof.

Preferably, said cell is selected from the group consisting of bacterial cells, yeast cells, insect cells or mammalian cells. The vector according to the invention is a plasmid or a virus, preferably a baculovirus, an adenovirus or a Semliki Forest virus.

The present invention concerns also the cell transformed by the vector according to the invention, said cell is preferably non-neuronal in origin and is selected from the group consisting of a COS-7 cell, a CHO cell, an LM(tk−) cell, an NIH-3T3 cell or a 1321N1 astrocytoma cell.

The present invention is also related to a nucleic acid probe comprising the nucleic acid molecule according to the invention, of at least 15 nucleotides capable of specifically hybridising with a unique sequence included in the sequence of the nucleic acid molecule encoding the receptor according to the invention. Said nucleic acid probe may be a DNA or an RNA molecule.

The invention concerns also an antisense oligonucleotide having a sequence capable of specifically hybridising to an mRNA molecule encoding the receptor according to the invention so as to prevent translation of said mRNA molecule or an antisense oligonucleotide having a sequence capable of specifically hybridising to the cDNA molecule encoding the receptor according to the invention.

Said antisense oligonucleotide may comprise chemical analogs of nucleotide or substances which inactivate mRNA, or be included in an RNA molecule endowed with ribozyme activity.

Another aspect of the present invention concerns a ligand (preferably an antibody) other than known molecules, especially the ATP, capable of binding to the receptor according to the invention and an anti-ligand (preferably also an antibody) capable of competitively inhibiting the binding of said ligand to the receptor according to the invention.

Preferably, said antibody is a monoclonal antibody directed to an epitope of the receptor according to the invention and present on the surface of a cell expressing said receptor.

The invention concerns also the pharmaceutical composition comprising an effective amount of oligonucleotide according to the invention, effective to decrease the activity of said receptor by passing through a cell membrane and binding specifically with mRNA encoding the receptor according to the invention in the cell so as to prevent its translation. The pharmaceutical composition comprises also a pharmaceutically acceptable carrier capable of passing through said cell membrane.

Preferably, in said pharmaceutical composition, the oligonucleotide is coupled to a substance, such as a ribozyme, which inactivates mRNA.

Preferably, the pharmaceutically acceptable carrier comprises a structure which binds to a receptor on a cell capable of being taken up by cell after binding to the structure. The structure of the pharmaceutically acceptable carrier in said pharmaceutical composition is capable of binding to a receptor which is specific for a selected cell type.

Preferably, said pharmaceutical composition comprises an amount of the antibody according to the invention effective to block the binding of a ligand to the receptor according to the invention and a pharmaceutically acceptable carrier.

The present invention concerns also a transgenic non human mammal overexpressing (or expressing ectopically) the nucleic acid molecule encoding the receptor according to the invention.

The present invention also concerns a transgenic non human mammal comprising a homologous recombination knockout of the native receptor according to the invention.

According to a preferred embodiment of the invention, the transgenic non human mammal whose genome comprises antisense nucleic acid complementary to the nucleic acid according to the invention is so placed as to be transcripted into antisense mRNA which is complementary to the mRNA encoding the receptor according to the invention and which hybridises to mRNA encoding said receptor, thereby reducing its translation. Preferably, the transgenic non human mammal according to the invention comprises a nucleic acid molecule encoding the receptor according to the invention and comprises additionally an inducible promoter or a tissue specific regulatory element.

Preferably, the transgenic non human mammal is a mouse.

The invention relates also to a method for determining whether a ligand as an agonist or an antagonist of the receptor according to the invention can be specifically bound to said receptor; said method comprising the steps of contacting a cell or a cell extract from cells transfected with a vector according to the invention and expressing the nucleic acid molecule encoding said receptor, possibly isolating a membrane fraction from the cell extract, contacting the ligand with the membrane fraction or with the cell under conditions permitting binding of said ligand to the receptor and detecting, possibly by means of a bioassay such as a modification in the second messenger concentration or a modification in the cellular metabolism (preferably determined by the acidification rate of the culture medium), an increase in the receptor activity, thereby determining whether the ligand binds to the receptor, possibly as an agonist or as an antagonist of said receptor.

Preferably, the second messenger assay comprises measurement of intracellular cAMP, intracellular inositol phosphate (IP3), intracellular diacylglycerol (DAG) concentration or intracellular calcium mobilisation.

Preferably, the cell used in said method is a mammalian cell non neuronal in origin, such as a COS-7 cell, a CHO cell, a LM(tk−) cell an NIH-3T3 cell or 1321N1 cell. In said method, the ligand is not previously known.

The invention is also related to the ligand isolated and detected by any of the preceding methods.

The present invention concerns also the pharmaceutical composition which comprises an effective amount of an agonist or an antagonist of the receptor according to the invention, effective to reduce the activity of said receptor and a pharmaceutically acceptable carrier.

The $P2Y_{11}$ transcripts (obtained from the nucleotidic sequence starting from (♦) in FIG. 1) are detectable in HL-60 human leukaemia cells. Expression of $P2Y_{11}$ receptor mRNA is increased by agents (ripnoic acid, DMSO) known to induce the granulocytic differenciations of HL-60 cells. However, the $P2Y_{11}$ transcripts could not be detected in mature neutrophils. Therefore, a first industrial application of the product according to the invention is the diagnostic of leukaemia, preferably by Northern blot analysis using the nucleotidic sequence encoding the $P2Y_{11}$ receptor according to the invention.

The present invention is also related to a diagnostic device or kit comprising the elements for the diagnostic of specific leukaemia, preferably HL-60 human leukaemia, comprising the receptor according to the invention, the nucleic acid sequence encoding said receptor, a nucleic acid probe comprising the nucleic acid molecule according to the invention of at least 15 nucleotides capable of specifically hybridising with a unique sequence included in the sequence of the nucleic acid molecule encoding the receptor according to the invention, such as an antisense oligonucleotide or a ligand such as an antibody, preferably a monoclonal antibody, capable of binding or competitively inhibiting the binding of a ligand to the receptor according to the invention. Said diagnostic device or kit could be used for the specific diagnostic or for the monitoring of the evolution of tumoral cells, especially leukaemia HL-60 cells.

Therefore, the previously described methods may be used for the screening of drugs (having advantageously anti-tumoral properties) which specifically bind to the receptor according to the invention.

Another industrial application of the present invention is related to the use of said drugs, preferably ligands or anti-ligands according to the invention, for the prevention and/or the treatment of specific diseases such as neutropenie or agranulocytose infections or cancer.

The invention is also related to the drugs isolated and detected by any of these methods.

The present invention concerns also a pharmaceutical composition comprising said drugs and a pharmaceutically acceptable carrier.

The invention is also related to a method of detecting expression of a receptor according to the invention by detecting the presence of mRNA coding for a receptor, which comprises obtaining total RNA or total mRNA from the cell and contacting the RNA or mRNA so obtained with the nucleic acid probe according to the invention under hybridising conditions and detecting the presence of mRMA hybridised to the probe, thereby detecting the expression of the receptor by the cell.

The hybridisation conditions above-described are preferably standard stringent conditions as described by Sambrook et al. (§9.47-9.51 in Molecular Cloning: A Laboratory Manual, Cold Spring Harbour, Laboratory Press, New York (1989)).

The present invention concerns also a method for diagnosing a predisposition to a disorder associated with the activity of the receptor according to the invention. Said method comprises:
a) obtaining nucleic acid molecules of subjects suffering from said disorder;
b) performing a restriction digest of said nucleic acid molecules with a panel of restriction enzymes;
c) electrophoretically separating the resulting nucleic acid fragments on a sized gel;
d) contacting the resulting gel with a nucleic acid probe capable of specifically hybridising to said nucleic acid molecule and labelled with a detectable marker;
e) detecting labelled bands which have hybridised to the said nucleic acid molecule labelled with a detectable marker to create a unique band pattern specific to subjects suffering from said disorder;
f) preparing nucleic acid molecules obtained for diagnosis by step a-e; and
g) comparing the unique band pattern specific to the nucleic acid molecule of subjects suffering from the disorder from step e and the nucleic acid molecule obtained for diagnosis from step f to determine whether the patterns are the same or different and to diagnose thereby predisposition to the disorder if the patterns are the same.

A last aspect of the present invention concerns a method of preparing the receptor according to the invention, which comprises:
a) constructing a vector adapted for expression in a cell which comprises the regulatory elements necessary for the expression of nucleic acid molecules in the cell operatively linked to nucleic acid molecule encoding said receptor so as to permit expression thereof, wherein the cell is selected from the group consisting of bacterial cells, yeast cells, insect cells and mammalian cells;
b) inserting the vector of step a in a suitable host cell;
c) incubating the cell of step b under conditions allowing the expression of the receptor according to the invention;
d) recovering the receptor so obtained; and
e) purifying the receptor so recovered, thereby preparing an isolated receptor according to the invention.

BRIEF DESCRIPTION OF THE DRAWINGS

FIG. 1A-E represents the nucleotide and deduced amino acid sequence of the new human P2Y receptor. The putative phosphorylation sites by protein kinase C or by calmodulin-dependent protein kinases are indicated respectively by a black circle (●) or a black diamond (♦). The potential N-glycosylation site is indicated by a black square (■).

Figure 1E:

DESCRIPTION OF A PREFERRED
EMBODIMENT OF THE PRESENT INVENTION

Experimental Procedures

Materials

Trypsin was from Flow Laboratories (Bioggio, Switzerland). Culture media, G418, fetal calf serum (FCS), restriction enzymes and Taq polymerase were purchased from GIBCO ERL (Grand Island, N.Y.). The radioactive products myo-D-[2-$^3$H]inositol (17.7 Ci/mmol) and [α$^{32}$P]ATP (800 Ci/mmol) were from Amersham (Ghent, Belgium). Dowex AG1X8 (formate form) was from Bio-Rad Laboratories (Richmond, Calif.) ATP, ADP, AMP, adenosine, UTP, UDP, $AP_4A$, $AP_6A$, all-trans retinoic acid (RA) and 12-O-tetradecanoylphorbol-3-acetate (TPA) were obtained from Sigma Chemical Co. (St. Louis, Mo.). 2-methylthio-ATP (2MeSATP), 2-methylthio-ADP (2MeSADP) and 8 (p-sulphenyl) theophylline were from Research Biochemicals International (Natick, Mass.). Forskolin was purchased from Calbiochem (Bierges, Belgium). Indomethacin and dimethyl sulfoxide (DMSO) were from Merck (Netherlands). Rolipram was obtained from the Laboratoires Jacques Logeais (Trappes, France). The HL-60 human cell line was obtained from the American Type Culture Collection (Rockville, USA). The human genomic DNA library was from Stratagene (La Jolla, Calif.). pEFIN3 is an expression vector obtained from Euroscreen (Brussels, Belgium). Multiple Human Tissues Northern blot (MTN) were from Clontech (Palo Alto, Calif.).

Cloning and Sequencing

A human placenta cDNA library was screened at moderate stringency with an [$\alpha^{32}P$] dATP labelled $P2Y_4$ receptor probe corresponding to a partial sequence covering the third to the seventh transmembrane segments. Three overlapping clones encoding a new G protein-coupled receptor were isolated, but did not contain the 3' end of the coding region. A human genomic DNA library was then screened with this partial sequence to obtain the complete sequence of this new receptor. The hybridization conditions for screening the two libraries were 6×SSC (1×SSC: 0.15 M NaCl, 0.015 M sodium citrate) and 40% formamide at 42° C. for 14 hours and the final washing conditions were 0.5×SSC, 0.1% SDS at 60° C. Four genomic clones were purified and shown to contain the 3' end of the open reading frame missing in the cDNA clones. The sequence was obtained on both strands after subcloning of overlapping restriction fragments in M13mp18 and M13mp19 using the Sanger dideoxy nucleotide chain termination method.

Northern Blot Analysis

Two blots of human organs (MTN I and MTN II: 2 µg polyA+ RNA/lane) and a blot containing total RNA from differentiated and undifferentiated HL-60 cells (10 µg of total RNA/lane) were hybridized with a probe corresponding to the new receptor in order to characterize its tissue distribution. The HL-60 cells were maintained in RPMI 1640 supplemented with 10% FCS, 5 mM L-glutamine, 50 U/ml penicillin and 50 µg/ml streptomycin at 37° C. with 5% $CO_2$. The HL-60 cells were incubated during six days with or without 1 µM retinoic acid or 1.25% DMSO or during eight hours with 25 nM TPA. The RNA from the differentiated or undifferentiated HL-60 cells was prepared with the RNeasy kit (Quiagen). The blots were prehybridized 8 hours at 42° C. in a 50% formamide, 2% SDS solution and hybridized for 18 hours in the same solution supplemented with the [$\alpha^{32}P$] labelled probe. The final washing conditions were 0.1×SSC and 0.1% SDS at 55° C. The blots were exposed during twelve days and visualized as an autoradiography or using the PhosphorImager SI (Molecular Dynamics).

Cell Culture and Transfection

The complete sequence of the new receptor according to the invention was subcloned between the Hind III and Nhe I sites of the bicistronic pEFIN3 expression vector. 1321N1 and CHO-K1 cells were transfected with the recombinant pEFIN3 plasmid or with the plasmid alone using the calcium phosphate precipitation method as described (19). The transfected cells were selected with 400 µg/ml G418 in complete medium (10% FCS, 100 units/ml penicillin, 100 µg/ml streptomycin and 2.5 µg/ml amphotericin B in Duibecco's modified Eagle's medium (DMEM)) two days after transfection and maintained in the same medium (10).

Inositol Phosphates (IP) Measurement

1321N1 cells were labelled for 24 hours with 10 mCi/ml [$^3H$] inositol in inositol free DMEM containing 5% FCS, antibiotics, amphotericin, sodium pyruvate and 400 µg/ml G418. Cells were washed twice with Krebs-Ringer Hepes (KRH) buffer of the following composition (124 mM NaCl, 5 mM KCl, 1.25 mM $MgSO_4$, 1.45 mM $CaCl_2$, 1.25 mM $KH_2PO_4$, 25 mM Hepes (pH:7.4) and 8 mM glucose) and incubated in the same medium for 30 min. The cells were then challenged by various nucleotides for 30 s. The incubation was stopped by the addition of an ice cold 3% perchioric acid solution. IP were extracted and separated on Dowex columns as previously described (20).

Cyclic AMP Measurements

Stably transfected CHO-K1 or 1321N1 cell lines were spread on Petri dishes (150.000 cells per dish) and cultured in Ham's F12 or DMEM medium containing 10% FCS, antibiotics, amphotericin, sodium pyruvate and 400 µg/ml G418. Cells were preincubated for 30 min in KRH buffer with Rolipram (25 µM) and incubated for different times in the presence of the agonists (15 min in most experiments). The incubation was stopped by the addition of 1 ml HCl 0.1 M. The incubation medium was dried up, resuspended in water and diluted as required. Cyclic AMP was quantified by radioimmunoassay after acetylation as previously described (21).

Results

Cloning and Sequencing

Figure 2:
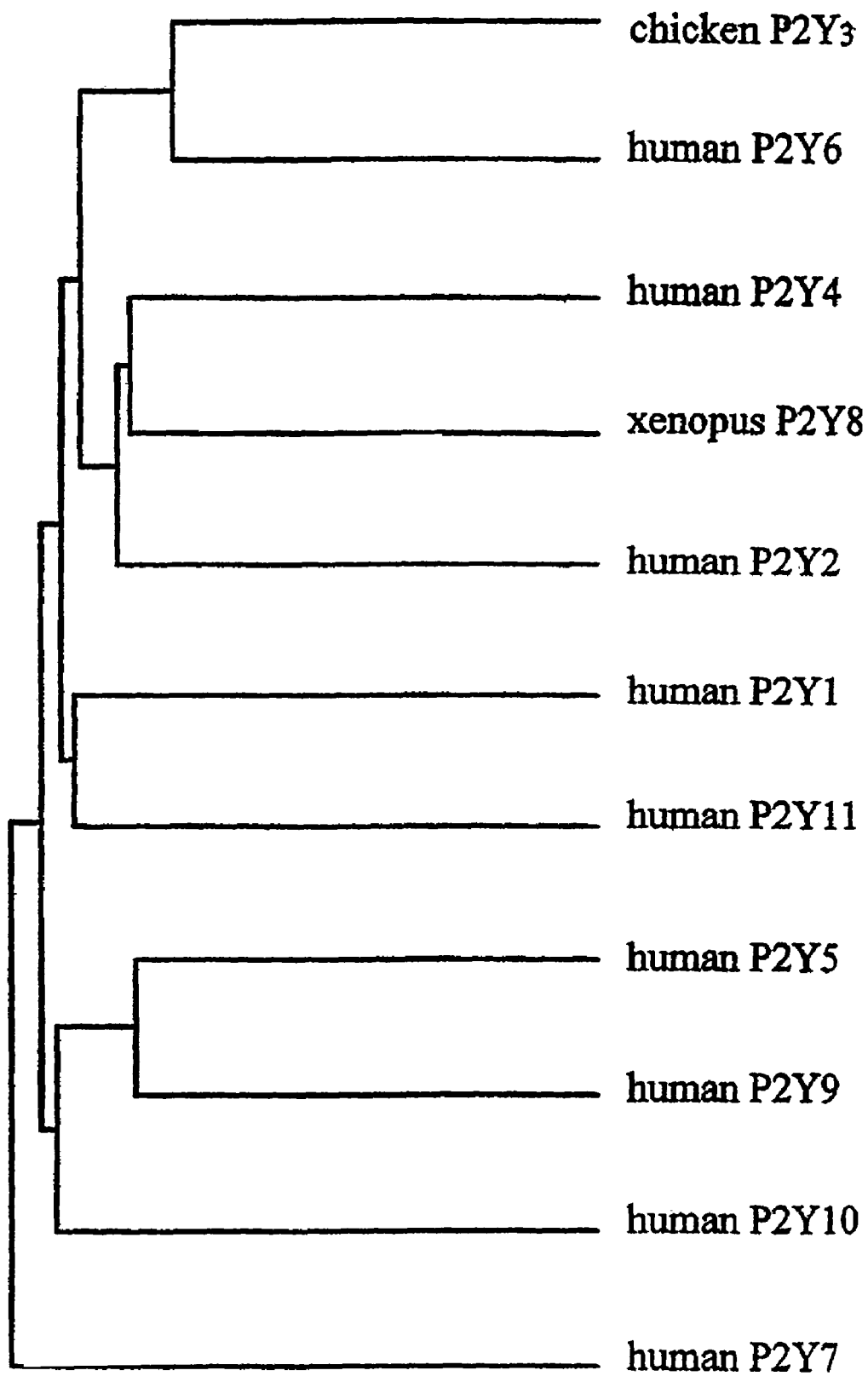
FIG. 2 represents dendrogram of the structural relatedness of the $P2Y_{11}$ receptor with the other P2Y subtypes. The plot was constructed using the multiple sequence alignment program Pileup of the GCG package. The $P2Y_5$-like published sequence (18) is identical to the $P2Y_9$ sequence submitted to the GenBank/EMBL Data Bank.

A human cDNA placenta library was screened at moderate stringency with a human $P2Y_4$ probe. Nine clones which hybridized weakly with the $P2Y_4$ probe were obtained, purified and analyzed. Six of them corresponded to the sequence of the $P2Y_6$ receptor (10) while three overlapping clones corresponded to a partial sequence encoding a new G protein-coupled receptor, displaying about 30% identity with the other P2Y receptors. The partial open reading frame started with an ATG-codon in a Kozak consensus but the 3' end was missing in all three cDNA clones. The Inventors screened a human genomic DNA library using this partial sequence as a probe. Four overlapping genomic clones were obtained. Mapping of the coding sequence and partial sequencing allowed to determine that the gene encoding the new receptor contains an intron interrupting the coding sequence at the 5' end of the gene. This intron separates the three first codons from the rest of the coding sequence. Beside these first codons, the four genomic clones contained the complete open reading frame including the 3' end missing in the cDNA clones. The full open reading frame appeared as 1113 base pairs (bp) long and encoded a protein of 371 amino acids containing one potential site for N-linked glycosylation and two potential sites for phosphorylation by protein kinase C or calmodulin-dependent protein kinases (FIG. 1). The new receptor, provisionally named $P2Y_{11}$, displays significant homologies with the other P2Y receptors (FIG. 2). In particular, 33% and 28% amino acid identity were observed respectively with the human $P2Y_1$ and $P2Y_2$ receptors.

Tissue Distribution of the New Receptor

Figure 3:
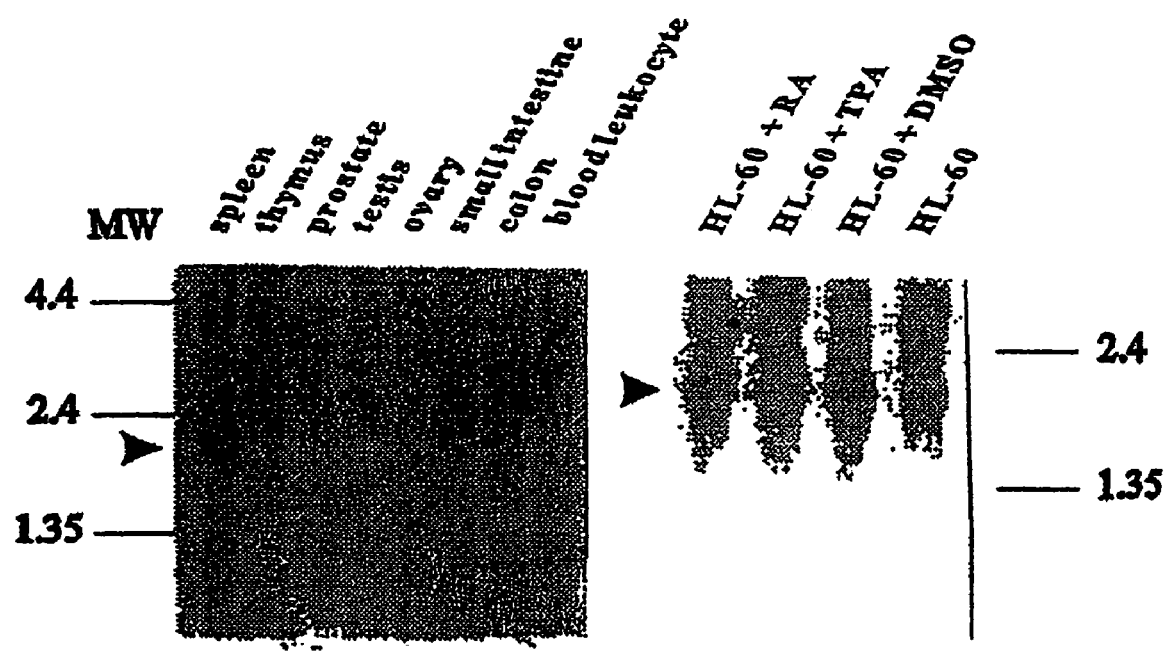
FIG. 3 represents Northern blot analysis of $P2Y_{11}$ messenger expression. Each lane of the MTN blot contains 2 μg of polyA$^+$ RNA from several human tissues. Each lane of the HL-60 blot contains 10 μg of total RNA from differentiated or undifferentiated HL-60 cells. Hybridization with the probe was performed as described under Materials and Methods. The pictures of the MTN II blot and the HL-60 blot were obtained respectively, from an autoradiography and from a PhosphorImager SI (Molecular Dynamics). The 2 kb-length $P2Y_{11}$ transcripts are indicated by a black arrow.

The tissue distribution of the new receptor transcripts was investigated by Northern blotting (FIG. 3) by using a probe corresponding to a partial sequence encoding transmembrane segments 3 to 7. The strongest signal was observed for human spleen and corresponded to a 2 kilobase (kb)-length messenger RNA (MTN II). A weaker signal was observed in small intestine (MTN II). All the lanes in MTN I (heart, brain, placenta, lung, liver, skeletal muscle, kidney, pancreas) were negative. The Inventors also detected specific 2 kb-length transcripts in HL-60 cells. The signal was very weak in the undifferentiated HL-60 cells but increased when the cells had been treated with retinoic acid or DMSO. No increase was observed when the HL-60 cells were stimulated with TPA. A weak non-specific hybridization with 18S rRNA was observed. These data were confirmed with a non-overlapping probe corresponding to the first 300 bp of the coding region, presenting limited homologies with the other P2Y subtypes.

Functional Expression of the New Receptor in 1321N1 Astrocytoma Cells

Figure 4A:
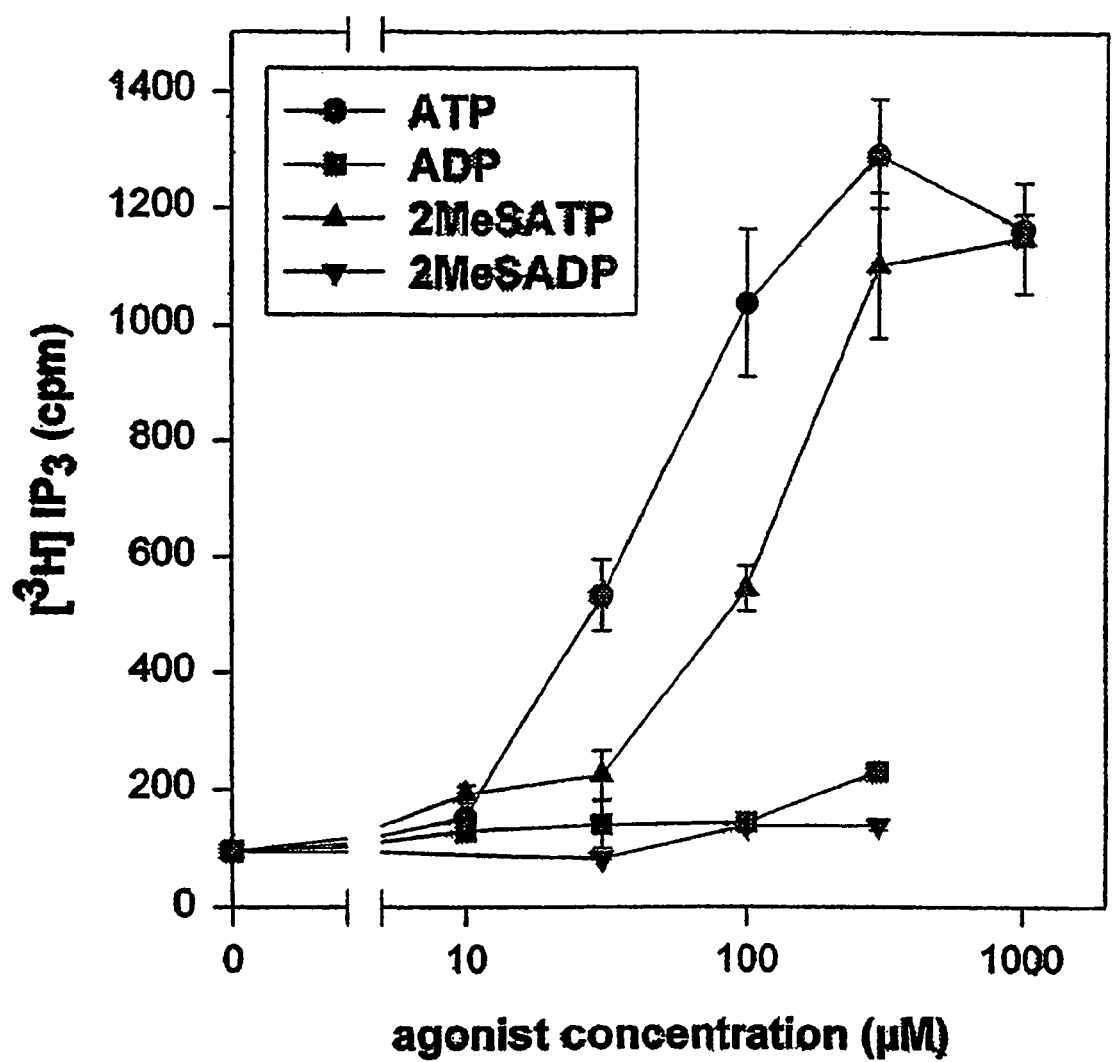
FIG. 4 represents concentration-action curves of several nucleotides on $IP_3$ and cAMP accumulation in cells transfected with the $P2Y_{11}$ receptor. 1321N1 and CHO-$K_1$ transfected cells were assayed for the accumulation of, respectively, $IP_3$ (A) or cAMP (B) in response to various concentrations of the following nucleotides: ATP, 2MeSATP, ADP and 2MeSADP. Incubation times were 30 s for $IP_3$ measurements and 15 min for cAMP assays. The data represent the means±S.D. of triplicate experimental points and are representative of two independent experiments.

The complete sequence of the new receptor was introduced in the pEFIN3 expression vector in order to transfect the 1321N1 astrocytoma cell line, used previously to characterize several P2Y subtypes (6, 10, 12). The pool of G418-resistant clones was tested for its functional response to several nucleotides. ATP (100 µM) induced a strong inositol trisphosphate ($IP_3$) accumulation in cells transfected with the recombinant plasmid, whereas ADP, AMP, adenosine, UTP, UDP, $AP_4A$ and $AP_6A$ were inactive at the same concentration. All nucleotides were totally inactive on the cells transfected with the vector alone. We then tested ATP, 2MeSATP, ADP and 2MeSADP in a large range of concentrations. As shown in FIG. 4A, ATP was the most potent agonist ($EC_{50}$ ATP=38±7 µM; $EC_{50}$ 2MeSATP=118±15 µM; means±range of two independent experiments). The effect of ADP and 2MeSADP were minimal. Pertussis toxin (50 ng/ml; 24 h pretreatment) had no effect on the ATP response, whereas a lower concentration of pertussis toxin was previously shown to abolish the response to UTP in $P2Y_4$ transfected 1321N1 astrocytoma cells (22). A response to ATP (10 µM) was also obtained following $[Ca^{2+}]_i$ measurements performed on the 1321N1 transfected cells while ADP was inactive at this concentration.

Functional Expression of the New Receptor in CHO-K1 Cells

Figure 4B:
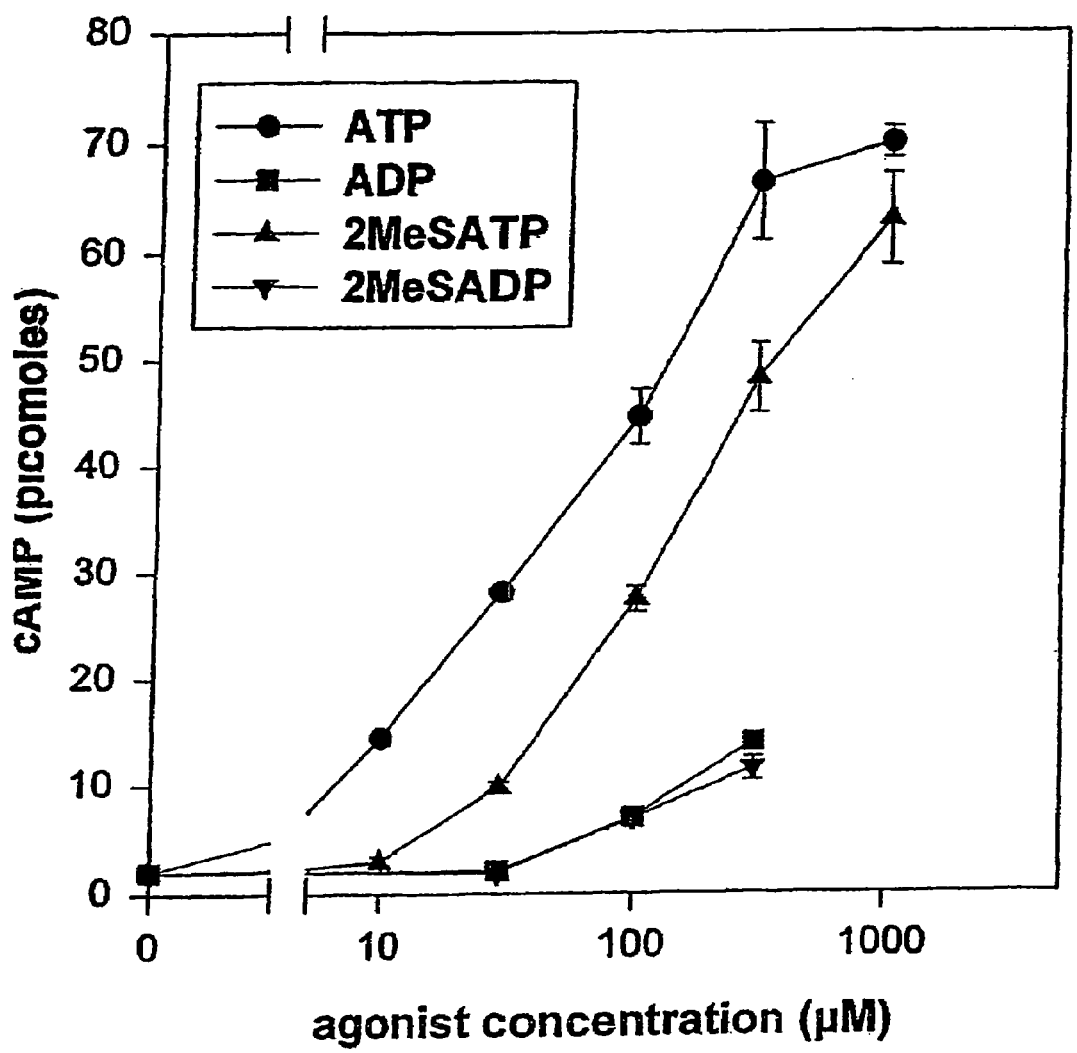

The 1321N1 cells transfected with the new receptor displayed a strong cAMP increase in response to ATP. A much lower but significant endogenous response due to the degradation of adenine nucleotides into adenosine was also obtained in the 1321N1 cells transfected with the vector alone. The CHO-K1 cells express an endogeneous $P2Y_2$ receptor coupled to the phosphoinositide pathway (23) but do not possess adenosine receptors coupled to adenylyl cyclase. We therefore used CHO-K1 cells in order to characterize the coupling of the new receptor to the cAMP pathway. A pool of G418 resistant CHO-K1 clones was first tested for its response to several nucleotides at a concentration of 100 µM. ATP was able to induce a strong increase in the cAMP content, whereas it was inactive on cells transfected with the vector alone. ADP, AMP, adenosine, UTP and UDP were completely inactive. Concentration-action curves were established for ATP, 2MeSATP, ADP and 2MeSADP (FIG. 4B). The rank order of potency was the same as in the inositol phosphate study on 1321N1 cells. The curves were obtained after 15 min of stimulation by the agonists; however a significant cAMP response to ATP was already obtained after 2 min of stimulation. The response to ATP (30 µM) was inhibited neither by indomethacin (10 µg/ml, present from 30 minutes before the stimulation and readded in the stimulation medium) nor by 8 (p-sulfophenyl) theophylline (100 µM).

The receptor according to the invention presents some structural peculiarities which differentiate it from some other P2Y subtypes. Concerning its gene structure, the coding sequence is interrupted by an intron. Comparison between the cDNA and the genomic DNA sequences has clearly demonstrated the absence of intron in the coding region of the human $P2Y_1$ receptor (24, 25), the rat $P2Y_2$ receptor (26) and the rat $P2Y_6$ receptor (11). In terms of protein structure, the second and third extracellular loops are significantly longer than those of the other P2Y receptors. The homology with the other subtypes is relatively weak (about 30%). The closest G-coupled receptor is the human $P2Y_1$ receptor (33%) which is also a receptor responsive to adenine nucleotides (3, 4). Mutagenesis experiments with the $P2Y_2$ receptor have identified three positively charged amino acids in the sixth and seventh transmembrane domains ($His^{262}$, $Arg^{265}$ and $Arg^{292}$), which play a crucial role in nucleotide binding (presumably by neutralizing the negative charge of the phosphate groups) (27). These three residues are conserved in this new receptor.

So far, eight P2Y receptor subtypes are described in the literature ($P2Y_1$-$22Y_8$). In addition, two sequences related to the $P2Y_5$ receptor and named $P2Y_9$ and $P2Y_{10}$, have been recently submitted to the GenBank/EMBL Data Bank. The $P2Y_9$ sequence is identical to that recently published under the name "$P2Y_5$-like" (18). Therefore the new receptor described in this paper might be called $P2Y_{11}$. However, it is already clear that the nomenclature needs a revision. It was recently demonstrated that the $P2Y_7$ receptor is actually a receptor for leukotriene $B_4$ (16) and there is no functional evidence that the $P2Y_5$ and related receptors ($P2Y_5$-like or $P2Y_9$, $P2Y_{10}$) are nucleotide receptors (17, 18).

Among the sixteen human organs tested by Northern blotting, $P2Y_{11}$ transcripts of 2 kb size were only detectable in spleen, and with lower intensity in small intestine. This distribution is reminiscent of that of the human $P2Y_6$ 1.7 kb-messenger. The observation of the expression of the $P2Y_{11}$ receptor in the HL-60 cell line shows that this expression was strongly increased following treatment by DMSO or retinoic acid, two agents known to induce the differentiation of these cells into granulocytes (28). On the contrary, TPA, which is known to induce the monocytic differentiation of the HL-60 cells (29), did not stimulate the expression of the $P2Y_1$, receptor. The confirmation of these data with a second probe of the $P2Y_{11}$ cDNA, that shares little similarity with other P2Y sequences, excludes possible cross-hybridization with another P2Y receptor transcript. In view of the Northern blots results, it is tempting to speculate that the $P2Y_{11}$ receptor is involved in the recently described accumulation of cAMP in ATP-stimulated HL-60 cells (30).

Among the P2Y receptors, the $P2Y_{11}$ subtype has the unique property to activate both the phosphoinositide and the cAMP pathways. Other cloned P2Y receptors are coupled to phospholipase C exclusively. The rank order of potency of agonists was the same for the two pathways. ATP was clearly much more potent than ADP. This difference may be even underestimated as a result of low level ATP contamination in ADP preparation or conversion of ADP into ATP during assays (4, 11). On the other hand, 2MeSATP had the same maximal effect than ATP but presented a lower potency, while 2MeSADP, a potent activator of the $P2Y_1$ and $P2Y_{2T}$ subtypes (4), was almost inactive. The $EC_{50}$ values were comparable to those obtained in the study concerning the effects of extracellular nucleotides on the cAMP accumulation in the HL-60 cells (30).

Stimulatory effects of adenine nucleotides on the cAMP pathway have been described in different cell types (31, 32). In most cases, the stimulatory effect of nucleotides was inhibited by xanthines. These data suffer from the fact that it is difficult to exclude that the effect of adenine nucleotides is mediated by their degradation into adenosine due to the ubiquitous presence of ectonucleotidases expressed at the cell surface. The cAMP study has been performed with CHO-K1 cells to avoid the endogeneous cAMP response to adenosine in the astrocytoma cell line. Neither in untransfected CHO-K1 cells nor in $P2Y_{11}$-transfected CHO-K1 cells did adenosine increase cAMP accumulation. Furthermore the cAMP response to ATP was insensitive to xanthine inhibition. It was also insensitive to indomethacin, indicating that is not mediated by the release of prostaglandins. It is unlikely that the cAMP response would be an indirect consequence of the calcium response since the use of ATP, which activates the phosphoinositide pathway by the activation of $P2Y_2$ endogeneous receptors, or the use of calcium ionophores in the CHO-K1 cells failed to stimulate cAMP accumulation (33). Therefore these data constitute the first strong evidence that a P$_2$ receptor can be coupled to the stimulation of adenylyl cyclase.

REFERENCES

1. Abbrachio, H. P. and Burnstock, G. (1994) *Pharmacol. Ther.* 64, 445-475.
2. Fredholm, B. B. et al. (1997) *Trends Pharmacol. Sci.* 18, 79-82.
3. Webb, T. E. et al. (1993) *FEBS Lett.* 324, 219-225.
4. Leon, C. et al. (1997) *FEBS Lett.* 403, 26-30.
5. Lustig, K. D. et al. (1993) *Proc. Natl. Acad. Sci. U.S.A.* 90, 5113-5117.
6. Parr, C. E. et al. (1994) *Proc. Natl. Acad. Sci. U.S.A.* 91, 3275-3279.
7. Bogdanov, Y. et al. (1997) *J. Biol. Chem.* 272, 12583-12590.
8. Webb, T. E. et al. (1996) *Mol. Pharmacol.* 50, 258-265.
9. Chang, K. et al. (1995) *J. Biol. Chem.* 270, 26152-26158.
10. Communi, D. et al; (1996) *Biochem. Biophys. Res. Commun.* 222, 303-308.
11. Nicholas, R. A. et al. (1996) *Mol. Pharmacol.* 50, 224-229.
12. Communi, D. et al. (1995) *J. Biol. Chem.* 270, 30849-30852.
13. Nguyen, T. et al. (1995) *J. Biol. Chem.* 270, 30845-30848.
14. Webb, T. E. et al. (1996) *Biochem. Biophys. Res. Commun.* 219, 105-110.
15. Akbar, G. K. M. et al. (1996) *J. Biol. Chem.* 271, 18363-18367.
16. Yokomizo, T. et al; (1997) *Nature* 387, 620-624.
17. Schachter, J. B. and Harden, T. K. (1997) *Br. J. Pharmacol.* 121, 338-344.
18. Janssens, R. et al. (1997) *Biochem. Biophys. Res. Commun.* 226, 106-112.
19. Velu, T. J. et al. (1989) *J. Cell. Biochem.* 39, 153-166.
20. Communi, D. et al. (1995) *Circ. Res.* 76, 191-198.
21. Brooker, G. et al. (1979) *Adv. Cyclic Nucleotide Res.* 10, 1-33.
22. Communi, D. et al. (1996) *Eur. J. Pharmacol.* 317, 383-389.
23. Iredale, P. A. and Hill, S. J. (1993) *Br. J. Pharmacol.* 110, 1305-1310.
24. Schachter, J. B. et al. (1996) *Br. J. Pharmacol.* 118, 167-173.
25. Janssens, R. et al. (1996) *Biochem. Biophys. Res. Commun.* 221, 588-593.
26. Godecke, S. et al. (1996) *Am. J. Physiol.* 270, C570-C577.
27. Erb, L. et al. (1995) *J. Biol. Chem.* 270, 4185-4188.
28. Breitman, T. R. et al. (1980) *Proc. Natl. Acad. Sci. USA* 77, 2936-2940.
29. Blaineau, C. et al. (1983) *Embo J.* 11, 2007-2012.
30. Jiang, L. et al. (1997) *Biochem. Biophys. Res. Commun.* 232, 626-630.
31. Matsuoka, I. et al. (1995) *Mol. Pharmacol.* 47, 855-862.
32. Song, S. L. and Chueh, S. H. (1996) *Brain Res.* 734, 243-251.
33. Thekkumkara, T. J. et al. (1995) *Mol. Cell Biochem.* 152, 77-86.

The invention claimed is:

1. An antibody which binds to a polypeptide comprising amino acid residues 424-795 of SEQ ID NO: 1, wherein said antibody binds to an epitope in amino acid residues 424-795 of SEQ ID NO:1.

2. The antibody of claim 1, wherein said antibody is an antagonist of said polypeptide.

3. The antibody of claim 1, wherein said antibody is a monoclonal antibody.

4. The antibody of claim 3, wherein said epitope is present on the surface of a cell expressing said polypeptide.

5. A pharmaceutical composition comprising the antibody of claim 1, and a pharmaceutically acceptable carrier.

* * * * *

SEQUENCE LISTING

```
<160> NUMBER OF SEQ ID NOS: 2

<210> SEQ ID NO 1
<211> LENGTH: 795
<212> TYPE: PRT
<213> ORGANISM: Homo sapiens

<400> SEQUENCE: 1

Met Gly Gln Ser Gly Arg Ser Arg His Gln Lys Arg Ala Arg Ala Gln
1               5                   10                  15

Ala Gln Leu Arg Asn Leu Glu Ala Tyr Ala Ala Asn Pro His Ser Phe
            20                  25                  30

Val Phe Thr Arg Gly Cys Thr Gly Arg Asn Ile Arg Gln Leu Ser Leu
        35                  40                  45

Asp Val Arg Arg Val Met Glu Pro Leu Thr Ala Ser Arg Leu Gln Val
    50                  55                  60

Arg Lys Lys Asn Ser Leu Lys Asp Cys Val Ala Val Ala Gly Pro Leu
65                  70                  75                  80

Gly Val Thr His Phe Leu Ile Leu Ser Lys Thr Glu Thr Asn Val Tyr
                85                  90                  95

Phe Lys Leu Met Arg Leu Pro Gly Gly Pro Thr Leu Thr Phe Gln Val
            100                 105                 110

Lys Lys Tyr Ser Leu Val Arg Asp Val Val Ser Ser Leu Arg Arg His
        115                 120                 125

Arg Met His Glu Gln Gln Phe Ala His Pro Pro Leu Leu Val Leu Asn
    130                 135                 140
```

```
Ser Phe Gly Pro His Gly Met His Val Lys Leu Met Ala Thr Met Phe
145                 150                 155                 160

Gln Asn Leu Phe Pro Ser Ile Asn Val His Lys Val Asn Leu Asn Thr
                165                 170                 175

Ile Lys Arg Cys Leu Leu Ile Asp Tyr Asn Pro Asp Ser Gln Glu Leu
            180                 185                 190

Asp Phe Arg His Tyr Ser Ile Lys Val Pro Val Gly Ala Ser Arg
        195                 200                 205

Gly Met Lys Lys Leu Leu Gln Glu Lys Phe Pro Asn Met Ser Arg Leu
    210                 215                 220

Gln Asp Ile Ser Glu Leu Leu Ala Thr Gly Ala Gly Leu Ser Glu Ser
225                 230                 235                 240

Glu Ala Glu Pro Asp Gly Asp His Asn Ile Thr Glu Leu Pro Gln Ala
            245                 250                 255

Val Ala Gly Arg Gly Asn Met Arg Ala Gln Gln Ser Ala Val Arg Leu
            260                 265                 270

Thr Glu Ile Gly Pro Arg Met Thr Leu Gln Leu Ile Lys Val Gln Glu
        275                 280                 285

Gly Val Gly Glu Gly Lys Val Met Phe His Ser Phe Val Ser Lys Thr
    290                 295                 300

Glu Glu Glu Leu Gln Ala Ile Leu Glu Ala Lys Glu Lys Lys Leu Arg
305                 310                 315                 320

Leu Lys Ala Gln Arg Gln Ala Gln Gln Ala Gln Asn Tyr Gln Arg Lys
            325                 330                 335

Gln Glu Gln Arg Glu Ala His Arg Lys Lys Ser Leu Glu Gly Met Lys
        340                 345                 350

Lys Ala Arg Val Gly Gly Ser Asp Glu Ala Ser Gly Ile Pro Ser
    355                 360                 365

Arg Thr Ala Ser Leu Glu Leu Gly Glu Asp Asp Glu Gln Glu Asp
        370                 375                 380

Asp Asp Ile Glu Tyr Phe Cys Gln Ala Val Gly Glu Ala Pro Ser Glu
385                 390                 395                 400

Asp Leu Phe Pro Glu Ala Lys Gln Lys Arg Leu Ala Lys Ser Pro Gly
            405                 410                 415

Arg Lys Arg Lys Arg Trp Glu Met Asp Arg Gly Ala Lys Ser Cys Pro
        420                 425                 430

Ala Asn Phe Leu Ala Ala Ala Asp Asp Lys Leu Ser Gly Phe Gln Gly
    435                 440                 445

Asp Phe Leu Trp Pro Ile Leu Val Glu Phe Leu Val Ala Val Ala
        450                 455                 460

Ser Asn Gly Leu Ala Leu Tyr Arg Phe Ser Ile Arg Lys Gln Arg Pro
465                 470                 475                 480

Trp His Pro Ala Val Val Phe Ser Val Gln Leu Ala Val Ser Asp Leu
            485                 490                 495

Leu Cys Ala Leu Thr Leu Pro Pro Leu Ala Ala Tyr Leu Tyr Pro Pro
        500                 505                 510

Lys His Trp Arg Tyr Gly Glu Ala Cys Arg Leu Glu Arg Phe Leu
    515                 520                 525

Phe Thr Cys Asn Leu Leu Gly Ser Val Ile Phe Ile Thr Cys Ile Ser
        530                 535                 540

Leu Asn Arg Tyr Leu Gly Ile Val His Pro Phe Phe Ala Arg Ser His
545                 550                 555                 560

Leu Arg Pro Lys His Ala Trp Ala Val Ser Ala Ala Gly Trp Val Leu
```

-continued

```
                565                 570                 575
Ala Ala Leu Leu Ala Met Pro Thr Leu Ser Phe Ser His Leu Lys Arg
            580                 585                 590

Pro Pro Gln Gln Gly Ala Gly Asn Cys Ser Val Ala Arg Pro Glu Ala
        595                 600                 605

Cys Ile Lys Cys Leu Gly Thr Ala Asp His Gly Leu Ala Ala Tyr Arg
    610                 615                 620

Ala Tyr Ser Leu Val Leu Ala Gly Leu Gly Cys Gly Leu Pro Leu Leu
625                 630                 635                 640

Leu Thr Leu Ala Ala Tyr Gly Ala Leu Gly Arg Ala Val Leu Arg Ser
            645                 650                 655

Pro Gly Met Thr Val Ala Glu Lys Leu Arg Val Ala Ala Leu Val Ala
            660                 665                 670

Ser Gly Val Ala Leu Tyr Ala Ser Ser Tyr Val Pro Tyr His Ile Met
        675                 680                 685

Arg Val Leu Asn Val Asp Ala Arg Arg Trp Ser Thr Arg Cys Pro
        690                 695                 700

Ser Phe Ala Asp Ile Ala Gln Ala Thr Ala Ala Leu Glu Leu Gly Pro
705                 710                 715                 720

Tyr Val Gly Tyr Gln Val Met Arg Gly Leu Met Pro Leu Ala Phe Cys
                725                 730                 735

Val His Pro Leu Leu Tyr Met Ala Ala Val Pro Ser Leu Gly Cys Cys
            740                 745                 750

Cys Arg His Cys Pro Gly Tyr Arg Asp Ser Trp Asn Pro Glu Asp Ala
            755                 760                 765

Lys Ser Thr Gly Gln Ala Leu Pro Leu Asn Ala Thr Ala Ala Pro Lys
    770                 775                 780

Pro Ser Glu Pro Gln Ser Arg Glu Leu Ser Gln
785                 790                 795

<210> SEQ ID NO 2
<211> LENGTH: 2427
<212> TYPE: DNA
<213> ORGANISM: Homo sapiens

<400> SEQUENCE: 2
gaattcggca cgaggaggcc tcgtggagga cacagcagca tgggacagtc agggaggtcc      60
cggcaccaga gcgcgcccg cgcccaggcg cagctccgca acctcgaggc ctatgccgcg      120
aacccgcact cgttcgtgtt cacgcgaggc tgcacgggtc gcaacatccg gcagctcagc      180
ctggacgtgc ggcgggtcat ggagccgctc actgccagcc gtctgcaggt tcgtaagaag      240
aactcgctga aggactgcgt ggcagtggct gggcccctcg gggtcacaca ctttctgatc      300
ctgagcaaaa cagagaccaa tgtctacttt aagctgatgc gcctcccagg aggccccacc      360
ttgaccttcc aggtgaagaa gtactcgctg gtgcgtgatg tggtctcctc actgcgccgg      420
caccgcatgc acgagcagca gtttgcccac ccaccccctcc tggtactcaa cagctttggc      480
ccccatggta tgcatgtgaa gctcatggcc accatgttcc agaacctgtt ccctccatc      540 aacgtgcaca aggtgaacct gaacaccatc aagcgctgcc tcctcatcga ctacaacccc      600
gactcccagg agctggactt ccgccactat agcatcaaag ttgttcctgt gggcgcgagt      660
cgcgggatga agaagctgct ccaggagaag ttccccaaca tgagccgcct gcaggacatc      720
agcgagctgc tggccacggg cgcggggctg tcggagagcg aggcagagcc tgacggcgac      780
cacaacatca cagagctgcc tcaggctgtc gctggccgtg gcaacatgcg ggcccagcag      840
```

```
agtgcagtgc ggctcaccga gatcggcccg cggatgacac tgcagctcat caaggtccag    900
gagggcgtcg gggagggcaa agtgatgttc cacagttttg tgagcaagac ggaggaggag    960
ctgcaggcca tcctggaagc caaggagaag aagctgcggc tgaaggcgca gaggcaggcc   1020
cagcaggccc agaatgtgca gcgcaagcag gagcagcggg aggcccacag aaagaagagc   1080
ctggagggca tgaagaaggc acgggtcggg ggtagtgatg aagaggcctc tgggatccct   1140
tcaaggacgg cgagcctgga gttgggtgag gacgatgatg aacaggaaga tgatgacatc   1200
gagtatttct gccaggcggt gggcgaggcg cccagtgagg acctgttccc cgaggccaag   1260
cagaaacggc ttgccaagtc tccagggcgg aagcggaagc ggtgggaaat ggatcgaggt   1320
gccaagtcct gccctgccaa cttcttggca gctgccgacg acaaactcag tgggttccag   1380
ggggacttcc tgtggcccat actggtggtt gagttcctgg tggccgtggc cagcaatggc   1440
ctggccctgt accgcttcag catccggaag cagcgcccat ggcacccgc cgtggtcttc    1500 tctgtccagc tggcagtcag cgacctgctc tgcgctctga cgctgccccc gctggccgcc   1560
tacctctatc cccccaagca ctggcgctat ggggaggccg cgtgccgcct ggagcgcttc   1620
ctcttcacct gcaacctgct gggcagcgtc atcttcatca cctgcatcag cctcaaccgc   1680
tacctgggca tcgtgcaccc cttcttcgcc cgaagccacc tgcgacccaa gcacgcctgg   1740
gccgtgagcg ctgccggctg ggtcctggcc gccctgctgg ccatgccac actcagcttc   1800 tcccacctga agaggccgcc gcagcagggg gcgggcaact gcagcgtggc caggcccgag   1860
gcctgcatca agtgtctggg gacagcagac cacgggctgg cggcctacag agcgtatagc   1920
ctggtgctgg cggggttggg ctgcggcctg ccgctgctgc tcacgctggc agcctacggc   1980
gccctcgggc gggccgtgct acgcagccca ggcatgactg tggccgagaa gctgcgtgtg   2040
gcagcgttgg tggccagtgg tgtggccctc tacgccagct cctatgtgcc ctaccacatc   2100
atgcgggtgc tcaacgtgga tgctcggcgg cgctggagca cccgctgccc gagctttgca   2160
gacatagccc aggccacagc agccctggag ctggggccct acgtgggcta ccaggtgatg   2220
cggggcctca tgcccctggc cttctgtgtc caccctctac tctacatggc cgcagtgccc   2280
agcctgggct gctgctgccg acactgcccc ggctacaggg acagctggaa cccagaggac   2340
gccaagagca ctggccaagc cctgcccctc aatgccacag ccgcccctaa accgtcagag   2400
ccccagtccc gtgagctgag ccaatga                                       2427
```